(12) United States Patent
Higgins et al.

(10) Patent No.: US 11,759,540 B2
(45) Date of Patent: Sep. 19, 2023

(54) PORTABLE DISINFECTION UNIT

(71) Applicant: CalyxPure, Inc., Houston, TX (US)

(72) Inventors: John C. Higgins, Houston, TX (US); Cody Renwick, Temecula, CA (US); Tim Gray, Oceanside, CA (US); Chris Fall, San Diego, CA (US); Bradley Craig Chapman, San Diego, CA (US)

(73) Assignee: CalyxPure, Inc., Houston, TX (US)

( * ) Notice: Subject to any disclaimer, the term of this patent is extended or adjusted under 35 U.S.C. 154(b) by 0 days.

(21) Appl. No.: 17/317,669

(22) Filed: May 11, 2021

(65) Prior Publication Data

US 2022/0362433 A1    Nov. 17, 2022

(51) Int. Cl.
*A61L 9/20* (2006.01)

(52) U.S. Cl.
CPC ............ *A61L 9/20* (2013.01); *A61L 2209/111* (2013.01); *A61L 2209/12* (2013.01); *A61L 2209/14* (2013.01); *A61L 2209/15* (2013.01)

(58) Field of Classification Search
None
See application file for complete search history.

(56) References Cited

U.S. PATENT DOCUMENTS

| | | | |
|---|---|---|---|
| 3,670,193 | A | 6/1972 | Thorington et al. |
| 3,992,646 | A | 11/1976 | Corth |
| 5,012,609 | A | 5/1991 | Ignatius et al. |
| 5,278,432 | A | 1/1994 | Ignatius et al. |

(Continued)

FOREIGN PATENT DOCUMENTS

| | | |
|---|---|---|
| CA | 2856725 | 6/2013 |
| CN | 201797809 | 4/2011 |

(Continued)

OTHER PUBLICATIONS

Argyroudi-Akoyunoglou et al., "Photoinduced Changes in the Chlorophyll a to Chlorophyll b Ratio in Young Bean Plants," Plant Physiology, Aug. 1970, 46(2), pp. 247-249.

(Continued)

*Primary Examiner* — Andrew Smyth
(74) *Attorney, Agent, or Firm* — Lewis & Reese, PLLC (57) ABSTRACT

A portable disinfecting apparatus with effective disinfection properties against pathogens, such as bacteria, fungi, and viruses is disclosed. Embodiments of the portable disinfecting apparatus include a portable sterilization box having at least one path configured to receive drawn air and to irradiate the drawn air with UV radiation along the path to produce disinfected air. The path may be provided using baffles that are configured, for example, in a serpentine or spiral configuration to provide a non-linear flow path for the air. The UV light sources, such as UV LEDs may be mounted on the baffles. Embodiments of the apparatus include an intake tube connected to the sterilization box for drawing air into the sterilization box from a point high within the room that is to be disinfected. The disinfected air is released from the sterilization box a point lower in the room. As the air is slightly heated during the disinfection process, drawing in air from high in the room and releasing the disinfected air lower in the room provides circulation and mixing of the disinfected air.

14 Claims, 5 Drawing Sheets

(56) References Cited

U.S. PATENT DOCUMENTS

| | | |
|---|---|---|
| 6,242,752 B1 | 6/2001 | Soma et al. |
| 6,791,259 B1 | 9/2004 | Stokes et al. |
| 7,658,891 B1 | 2/2010 | Barnes |
| 8,074,397 B2 | 12/2011 | Yoneda |
| 8,297,782 B2 | 10/2012 | Bafetti |
| 8,302,346 B2 | 11/2012 | Hunt et al. |
| 8,398,264 B2 | 3/2013 | Anderson |
| 8,453,376 B2 | 6/2013 | Chen |
| 8,476,844 B2 | 7/2013 | Hancock et al. |
| 8,508,204 B2 | 8/2013 | Deurenbeg et al. |
| 9,039,966 B2 | 5/2015 | Anderson et al. |
| 9,046,227 B2 | 6/2015 | Aurelien |
| 9,145,590 B2 | 9/2015 | Evans et al. |
| 9,162,077 B2 | 10/2015 | Nigola et al. |
| 9,333,274 B2 | 5/2016 | Peterson |
| 9,368,695 B2 | 6/2016 | Aurelien |
| 9,439,989 B2 | 9/2016 | Lalicki |
| 9,581,310 B2 | 2/2017 | Wu et al. |
| 9,681,515 B2 | 6/2017 | Rantala |
| 9,750,105 B2 | 8/2017 | Rantala |
| 9,938,165 B2 * | 4/2018 | Taghipour ............... C02F 1/325 |
| 10,104,740 B2 | 10/2018 | Rantala |
| 10,398,000 B2 | 8/2019 | Rantala |
| 10,440,900 B1 | 10/2019 | Higgins |
| 2003/0124023 A1 | 7/2003 | Burgess et al. |
| 2004/0008523 A1 | 1/2004 | Butler |
| 2005/0055070 A1 | 3/2005 | Jones et al. |
| 2005/0207159 A1 | 9/2005 | Maxik |
| 2006/0022582 A1 | 2/2006 | Radkov |
| 2006/0071589 A1 | 4/2006 | Radkov |
| 2006/0186377 A1 | 8/2006 | Takahashi et al. |
| 2006/0261742 A1 | 11/2006 | Ng et al. |
| 2006/0262545 A1 | 11/2006 | Piepgras et al. |
| 2006/0284199 A1 | 12/2006 | Matheson |
| 2008/0008620 A1 | 1/2008 | Alexiadis |
| 2008/0245788 A1 | 10/2008 | Choong et al. |
| 2008/0278927 A1 | 11/2008 | Li et al. |
| 2008/0305004 A1 | 12/2008 | Anderson et al. |
| 2008/0315217 A1 | 12/2008 | Van Der Wel |
| 2009/0018621 A1 | 1/2009 | Vogler et al. |
| 2009/0034236 A1 | 2/2009 | Reuben |
| 2009/0231832 A1 | 9/2009 | Zukauskas et al. |
| 2009/0267484 A1 | 10/2009 | Kasakura et al. |
| 2010/0001648 A1 | 1/2010 | De Clercq et al. |
| 2010/0121420 A1 | 5/2010 | Fiset et al. |
| 2010/0232135 A1 | 9/2010 | Munehiro et al. |
| 2010/0244724 A1 | 9/2010 | Jacobs et al. |
| 2010/0246169 A1 | 9/2010 | Anderson et al. |
| 2012/0068615 A1 | 3/2012 | Duong et al. |
| 2012/0099303 A1 | 4/2012 | Li et al. |
| 2012/0281408 A1 | 11/2012 | Owen et al. |
| 2012/0286304 A1 | 11/2012 | LeToquin et al. |
| 2012/0320607 A1 | 12/2012 | Kinomoto et al. |
| 2013/0077299 A1 | 3/2013 | Hussell et al. |
| 2013/0139437 A1 | 6/2013 | Maxik |
| 2013/0194795 A1 | 8/2013 | Onaka |
| 2013/0313516 A1 | 11/2013 | David et al. |
| 2013/0313546 A1 | 11/2013 | Yu |
| 2013/0318869 A1 | 12/2013 | Aikala |
| 2013/0320299 A1 | 12/2013 | Li |
| 2014/0034991 A1 | 2/2014 | McKenzie et al. |
| 2014/0152194 A1 | 6/2014 | Beyer |
| 2014/0254131 A1 | 9/2014 | Osinski et al. |
| 2014/0328046 A1 | 11/2014 | Aanegola et al. |
| 2015/0014715 A1 | 1/2015 | Hsing Chen et al. |
| 2015/0049459 A1 | 2/2015 | Peeters et al. |
| 2015/0083221 A1 | 3/2015 | Boonekamp et al. |
| 2015/0129781 A1 | 5/2015 | Kretschmann |
| 2015/0182646 A1 | 7/2015 | Anderson et al. |
| 2015/0196002 A1 | 7/2015 | Friesth |
| 2015/0342125 A1 | 12/2015 | Krijn et al. |
| 2016/0015840 A1 | 1/2016 | Gordon |
| 2016/0030610 A1 | 2/2016 | Peterson et al. |
| 2016/0088802 A1 | 3/2016 | Nicole et al. |
| 2016/0249810 A1 | 9/2016 | Darty et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2018/0147417 A1 | 5/2018 | Rantala |
| 2018/0224093 A1 | 8/2018 | Dutta et al. |
| 2019/0113219 A1 | 4/2019 | Niemiec et al. |
| 2019/0292315 A1 | 9/2019 | Niemiec et al. |
| 2020/0009286 A1 | 1/2020 | Zarcone et al. |
| 2020/0038542 A1 * | 2/2020 | Franklin ............... H01L 33/507 |
| 2022/0062488 A1 * | 3/2022 | Morgan-Lange .... B01J 35/0033 |
| 2022/0062489 A1 * | 3/2022 | Morgan-Lange ........ B01J 23/50 |

FOREIGN PATENT DOCUMENTS

| | | | | |
|---|---|---|---|---|
| CN | 103947469 | | 7/2014 | |
| CN | 103947470 | | 7/2014 | |
| CN | 104056289 | | 9/2014 | |
| CN | 107661532 A | * | 2/2018 | ............. A61L 9/145 |
| CN | 107661532 A | | 2/2018 | |
| CN | 109827261 A | * | 5/2019 | |
| CN | 111494695 A | * | 8/2020 | |
| CN | 111494695 A | | 8/2020 | |
| CN | 112057662 A | | 12/2020 | |
| EP | 2554583 | | 2/2013 | |
| JP | S6420034 | | 1/1989 | |
| JP | 2003339845 | | 12/2003 | |
| KR | 1020130125436 | | 11/2013 | |
| KR | 1020170114678 | | 10/2017 | |
| KR | 102042655 | | 11/2019 | |
| WO | 2001/014012 | | 3/2001 | |
| WO | 2002/067660 | | 9/2002 | |
| WO | 2003/063902 | | 8/2003 | |
| WO | 2004/033028 | | 4/2004 | |
| WO | 2006/100303 | | 9/2006 | |
| WO | 2006/126482 | | 11/2006 | |
| WO | 2007/012875 | | 2/2007 | |
| WO | 2007/049180 | | 5/2007 | |
| WO | 2009/045107 | | 4/2009 | |
| WO | 2009/056838 | | 5/2009 | |
| WO | 2013/141824 | | 9/2013 | |
| WO | 2014/188303 | | 11/2014 | |
| WO | 2015/066099 | | 5/2015 | |
| WO | 2016/019029 | | 2/2016 | |

OTHER PUBLICATIONS

Beelmann et al., "Post-harvest Vitamin D Enrichment of Fresh Mushrooms," HAL Project # MU07018, Apr. 30, 2009, Penn State University.

Carvalho et al., "Sequential Light Programs Shape Kale (*Brassica napus*) Sprout Appearance and Alter Metabolic and Nutrient Content," Horticulture Research 1, Article No. 8, 2014.

Eytan et al., "Changes in Photosystem I Activity and Membrane Organization During Degreening and Greening of a Chlamydomonas Reinhardi Mutant, y-1," The Journal of Biological Chemistry, vol. 249, No. 3, Issue of Feb. 10, , p. 738-744, 1974.

Kleuter et al., "Photosynthesis in Cucumbers with Pulsed or Continuous Light," Transactions of the ASABE, 23(2): 0437-0442, 1980.

Lefsrud et al., "Irradiance from Distinct Wavelength Light-Emitting Diodes Affect Secondary Metabolites in Kale," HortScience, vol. 43, No. 7, pp. 2243-2244, 2008.

Nicklisch, Andreas, "Growth and Light Absorption of Some Planktonic Cyanobacteria, Diatoms and Chlorphyceae Under Stimulated Natural Light Fluctuations," Journal of Plankton Research, vol. 20, Issue 1, pp. 105-119, 1998.

Olle et al., "The Effects of Light-Emitting Diode Lighting on Greenhouse Plant Growth and Quality," Agricultural and Food Science, vol. 22, No. 2, pp. 223-234, 2013.

Sforza et al., "Adjusted Light and Dark Cycles Can Optimize Photosynthetic Efficiency in Algae Growing in Photobioreactors," PLos ONE, 7(6): e38975, 2012.

(56) References Cited

OTHER PUBLICATIONS

Tennessen et al. "Efficiency of Photosynthesis in Continuous and Pulsed Light Emitting Diode Irradiation," Photosynthesis Research, 44(3), pp. 261-269, 1995.

Vänninen et al. "Prospecting the Use of Artificial Lighting for Integrated Pest Management," ISHS Acta Horticulturae, 956, pp. 593-608, 2010.

Yeh et al., "High-Brightness LEDs—Energy Efficient Lighting Sources and their Potential in Indoor Plant Cultivation," Renewable and Sustainable Energy Reviews, vol. 13, Issue 8, pp. 2175-2180, 2009.

R.M. Tomb et al., "New Proof-of-Concept in Viral Inactivation: Virucidal Efficacy of 405 nm Light Against Feline Calicivirus as a Model for Norovirus Decontamination," Food & Environmental Virology, vol. 9(2), 23 pages (2017).

A.J. DeLucca et al., "Blue Light (470 nm) Effectively Inhibits Bacterial and Fungal Growth," Letters in Applied Biology, vol. 55., pp. 460-466 (2012).

C.D. Ltyle et al., "Predicted Inactivation of Viruses of Relevance to Biodefense by Solar Radiation," J. Virology (vol. 79 (22), pp. 14244-14252 (2005).

K. Bergmann, "UV-C Irradiation: A New Viral Inactivation Method for Biopharmaceuticals," America Pharmaceutical Review, vol. 17(6) (Nov. 2014).

Pinter, Matt, et al., "IEC/EN 62471 (Eye Safety) for LED Lighting Products—Standards for Eye and Skin Safety," Smart Vision Lights, 2009, 4 pages.

Neumark, et al., "Wide Bandgap Light Emitting Materials and Devices," John Wiley & Sons, 2008, 50 pages.

Dai, Tianhong, et al., "Blue Light for Infectious Diseases: Propionibacterium Acnes, Helicobacter Pylori, and Beyond?" National Institutes of Health—Drug Resist Update, Aug. 2012, 15(4), pp. 223-236.

Daicho, Hisayoshi, et al., "A Novel Phosphor for Glareless White Light-Emitting Diodes," Nature Communications, 3:1132, Oct. 16, 2012, 8 pages.

Setlur, Anant A., "Phosphors for LED-based Solid-State Lighting," The Electrochemical Society Interface, Winter 2009, 5 pages.

TRI-R Project Brochure, Toshiba Materials Co., LTD., retrieved on Aug. 18, 2017, 16 pages.

Extended European Search Report regarding corresponding EP Patent Application No. 22165402.3, dated Oct. 6, 2022.

\* cited by examiner

PORTABLE DISINFECTION UNIT

FIELD OF THE INVENTION

This application relates to a portable apparatus having the ability to disinfect pathogens such as bacteria, fungi, and viruses.

INTRODUCTION

The COVID-19 global health crisis highlights the need for methods and systems for disinfecting pathogens in the air, especially in indoor settings, such as homes, offices, school rooms, and the like. Various systems that use ultraviolet (UV) irradiation to disinfect/deactivate pathogens, such as the novel coronavirus (SARS-CoV-2) that is responsible for COVID-19, have been proposed. One example is described in U.S. patent application Ser. No. 16/846,816, filed Apr. 13, 2020, and entitled "Light Fixture Having a Fan and Ultraviolet Sterilization," the entire contents of which are incorporated herein by reference. That patent application (referred to herein as "the '816 Application") describes a light fixture having a light box configured to provide white room lighting to a room and also having a pathogen sterilizing box, typically configured on top of the light box. The fixture includes a fan to continuously draw air into the sterilization box, where the air is irradiated with UV radiation provided from UV LED chips. The sterilized air is released back into the room. The white light provided by the light box may also be provided using LEDs. According to some embodiments described in the '816 Application, the LEDs provide illumination that have significant emission peaks at 405 nm and 470 nm, which is also useful for pathogen inactivation.

While the sterilizing light fixture described in the '816 Application is highly effective, the inventors have recognized the need for more portable disinfecting units.

DETAILED DESCRIPTION

Figure 1:
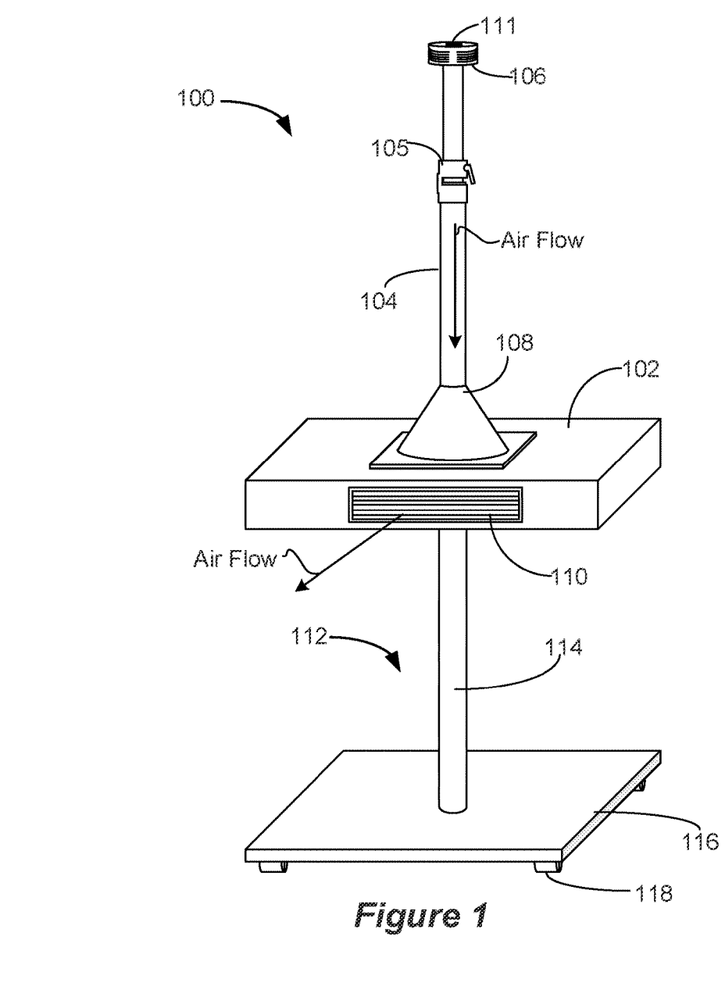
FIG. 1 shows an embodiment of a portable disinfecting unit.

FIG. 1 illustrates an embodiment of a portable disinfecting unit 100 for sterilizing/disinfecting room air. The portable disinfecting unit 100 comprises a sterilization box 102. As explained in more detail below, room air is drawn into the sterilization box 102, where it is disinfected using ultraviolet (UV) radiation. The sterilized air is released back into the room. Note that the sterilization box 102 does not need to be box-shaped as shown, it may instead be understood as any compartment, region, or volume, however shaped and sized. According to one embodiment, the sterilization box 102 is box-shaped, having dimensions of about 2 feet wide, 2 feet deep, and about 4.5-5 inches tall. Other sizes, such as 2×4 feet may be used. The walls of the sterilization box 102 may generally any material, for example, metal, fiberglass, plastic, or the like.

In the illustrated embodiment, room air is drawn into the sterilization box 102 via an intake tube 104. The intake tube 104 is sized in length to capture air from toward the top part of the room. According to some embodiments, it is beneficial to draw the room air from high in the room, particularly from a height in the room above the occupants' heads. As the room air passes through the sterilization box and is sterilized the air is slightly heated. Releasing the sterilized air from the sterilization box lower in the room provides circulation of the air in the room because the slightly heated sterilized air tends to rise. According to some embodiments, the intake tube is at least two feet in length, at least four feet in length, at least six feet in length, or at least eight feet in length. According to some embodiments, the length of the intake tube 104 may adjustable. For example, the intake tube 104 may be telescoping and may comprise clamps or locks 105 to hold the adjusted tube at the desired length. According to some embodiments, the length of the intake tube may be adjustable from a length of about four feet to a length of about eight feet. The intake tube 104 may generally comprise any suitable material, such as metal, plastic, fiberglass, polyvinyl chloride (PVC), or the like. The intake tube 104 may include an intake vent 106 at the distal end, as illustrated. The intake tube 104 may be attached to the sterilization box 102 using a flange 108 as illustrated. Other configurations for attaching the intake tube 104 to the sterilization box 102 will be apparent to a person of skill in the art.

As explained below, room air that is draw into the sterilization box 102 is sterilized/disinfected using UV light within the sterilization box and the sterilized/disinfected air is provided back into the room via one or more exhaust vents 110. Generally, any number of exit vents 110 may be used, depending on the configuration of the sterilization box 102. According to some embodiments, the sterilization unit 100 may include a sensor system 111 configured to sense various aspects of the room environment. In FIG. 1 the sensor system 111 is attached to the intake vent 106. However, the sensor system could be attached elsewhere on the sterilization unit 100. Moreover, the sensor system may be located remotely from the sterilization unit, for example, within the ceiling of the room, in which case the sterilization unit may be configured to communicate wirelessly with the sensor system, as explained in more detail below.

In the illustrated embodiment, the sterilization box 102 is supported on a moveable stand 112. The illustrated moveable stand comprises a support 114 and a base 116. The support 114 can generally be of any shape or configuration capable of supporting the sterilization box. The illustrated support 114 comprises a cylinder or tube. According to some embodiments, the sterilization box 102 may connect directly to the support 114, for example, by bolting or otherwise affixing to the support. According to other embodiments, the support may include a shelf or other surface (not shown) upon which the sterilization box may sit. The base 116 can be generally any configuration, as will be apparent to a person of skill in the art. According to some embodiments, the base 116 may comprise wheels or casters 118. Note that some embodiments of the portable sterilization unit 100 may not include a stand 112, but may instead be configured to sit on the floor and/or on some other piece of furniture, such as a desk or table, etc.

Figure 2:
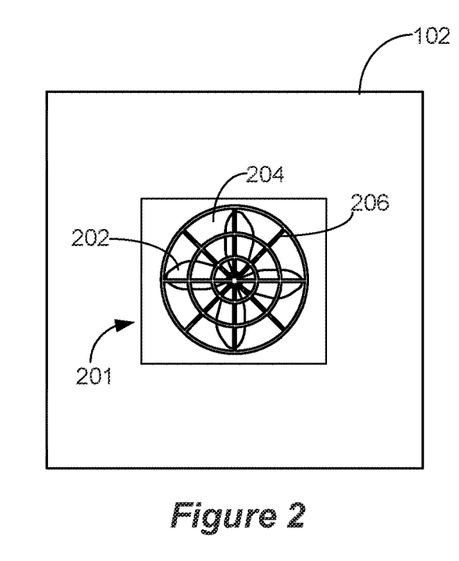
FIG. 2 shows a top view of a sterilization box.

FIG. 2 illustrates a top vies of the sterilization box 102 having the intake tube 104 and flange 108 removed. As shown, the sterilization box 102 includes a fan assembly 201 configured within a hole 204 in the top cover of the sterilization box. The hole 204 acts as an air intake port for the sterilization box 102. In the illustrated embodiment the fan assembly 201 comprises a fan 202 covered by a grate 206. The fan assembly 201 also includes a fan motor 208 (shown in FIG. 3). The fan 202 is configured to draw room air through the intake tube 104 and into the sterilization box 102. The fan assembly may be attached to the top surface of the sterilization box using screws, or the like. Note that while the fan assembly 201 is installed in the top surface of the sterilization box 102 in the illustrated embodiment, the fan/fan assembly could be stalled elsewhere in the air flow path, for example, at or near the exit vent(s) 110.

Figure 3:
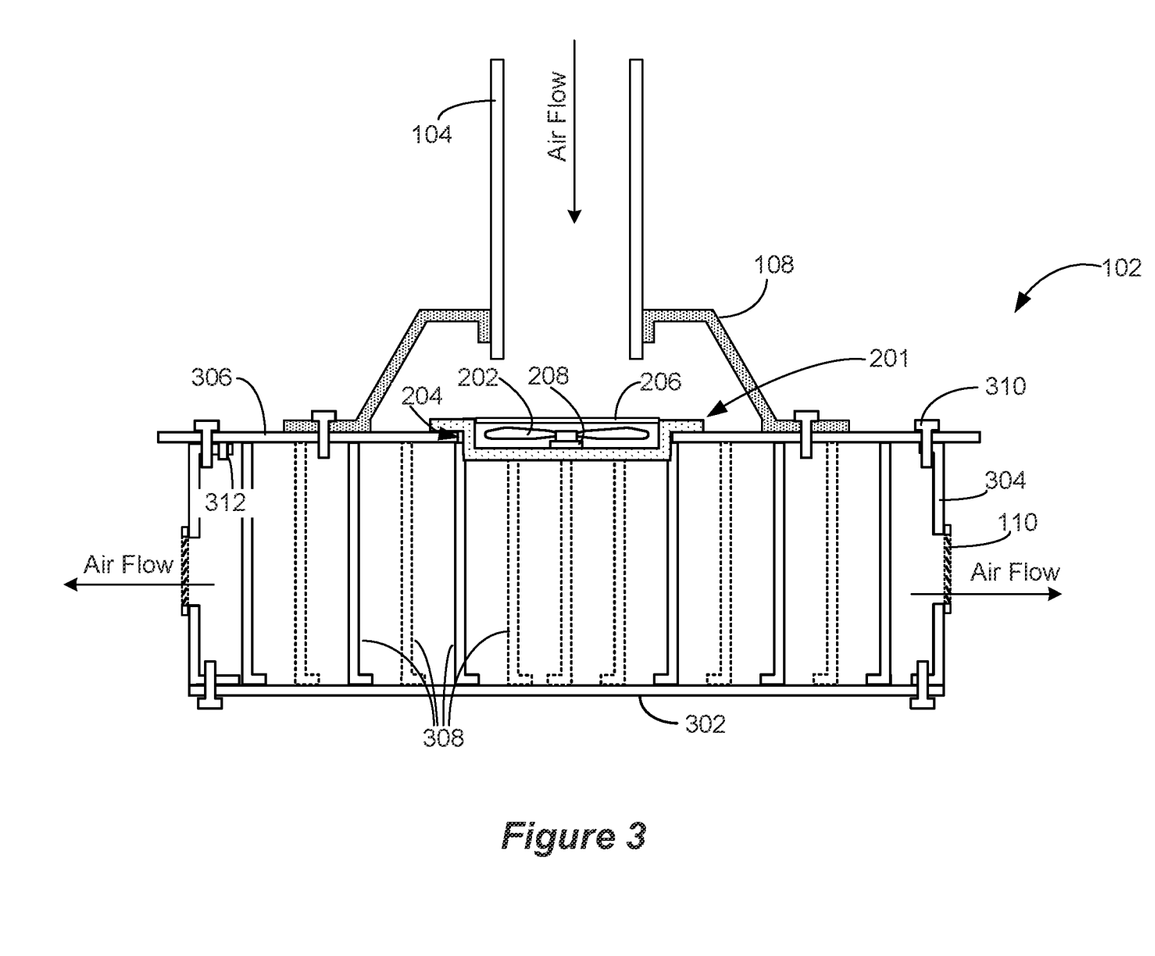
FIG. 3 shows a cross section of the sterilization box.

FIG. 3 shows a cross sectional view of the sterilization box 102. The sterilization box 102 includes a bottom surface 302, side surfaces 304, and a top cover 306. The inside of the sterilization box 102 includes baffles 308 which direct the air flow in a non-linear path and ultimately to exit vents 110 formed in one or more of the side surfaces 304. As will be explained in further detail later, these baffles 308 include UV LED chips to irradiate the air flow as it follows this non-linear path, which is described subsequently with respect to FIG. 4. The baffles 308 preferably comprise a metallic material, and may be affixed to the bottom surface 302. For example, the bottom edges of the baffles 308 can be bent as shown and affixed to the bottom surface 302 by spot welding, the use or screws, or the use of adhesives. The side surfaces 304 may be similarly attached to the bottom surface 302. In another example not shown, the baffles 308 may be integrated as a single piece, which can then be dropped into the sterilization box 102 during its assembly and affixed in place as necessary.

Components of the sterilization box 102 may be coated with antimicrobial or reflective materials. For example, the interior surfaces of the sterilization box may be coated with titanium dioxide. As well as having antimicrobial properties, titanium dioxide is highly reflective, thus encouraging reflection of the UV radiation within the UV sterilization box 102. This is preferred to absorption of the UV radiation, because absorption removes useful energy that could otherwise be used for disinfection of pathogens. In one example, the coating can comprise Paint Shield®, manufactured by Sherwin Williams. Such a coating can be applied to the vertical surfaces of the baffles 308, and could also be applied to the underside of the top cover 306, and the top side of the bottom surface 302.

The top cover 306 may be affixed to the side surfaces 304 using screws 310. This allows the top cover 306 to be removed to perform maintenance, such as to clean or remove the baffles 308 or to repair or replace system electronics, as explained subsequently. Likewise, the flange 108 may be affixed to the top cover 306 using screws. The top cover 306 can be affixed to the UV sterilization box 102 using other methods which allow it to be opened and reclosed for maintenance purposes.

The sterilization box 102 may include a safety switch 312 designed to cut power to the UV LED chips when the top cover 306 is removed. This is to prevent accidental UV exposure to persons who may be assembling or maintaining the sterilization box 102. This switch 103 can be provided in the sterilization box in different ways, but as shown the switch is mounted to the top flange of the side surface 304. As one skilled will understand, switch 312 includes a contact surface that will be depressed by the top cover 306 when it is connected to the UV sterilization box, thus closing the switch 312 and enabling the UV LED chips to receive power. When the top cover 306 is removed, the contact surface is not depressed and switch 312 is thus opened to prevent activation of the UV LED chips. Operation of the safety switch 312 is discussed further below with reference to FIG. 5.

Figure 4:
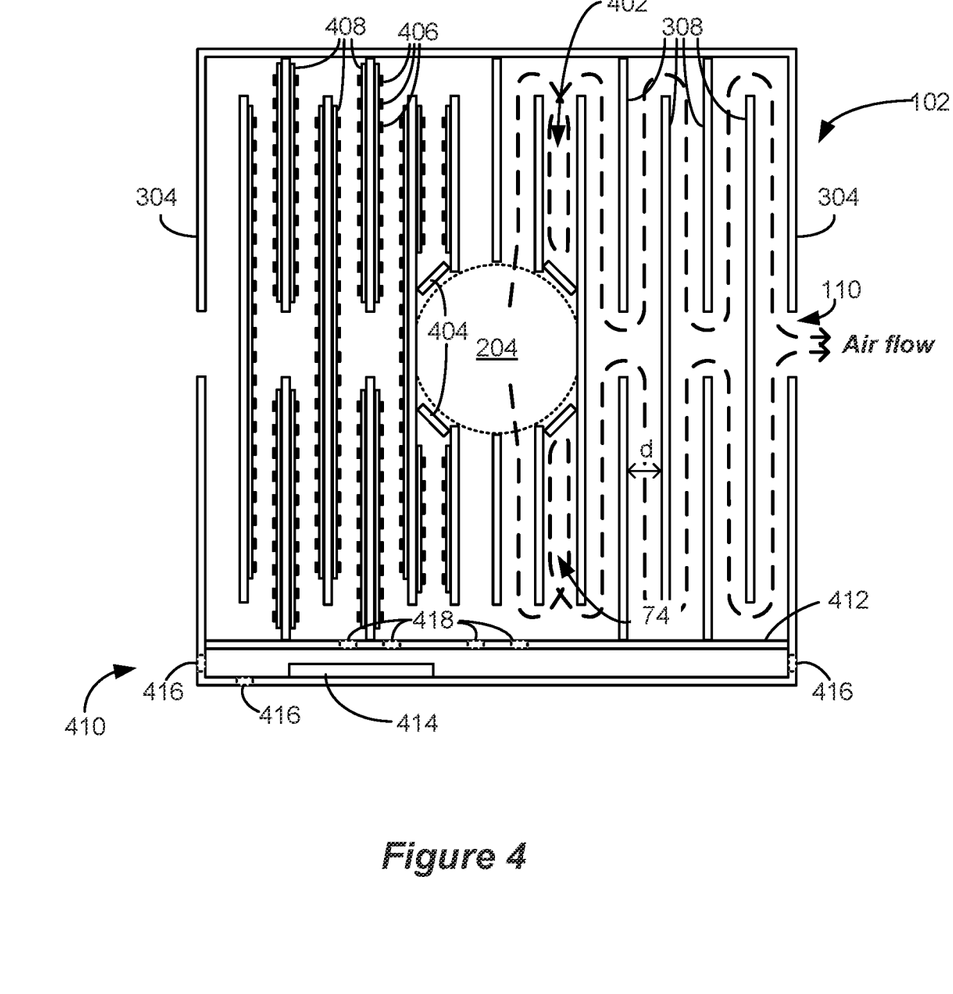
FIG. 4 shows a top-down view of the sterilization box having the top cover removed and also shows a baffle.

As shown in FIGS. 3 and 4, the top surface 306 of the sterilization box 102 has a hole 204, which promotes air flow from the fan 202 into the UV sterilization box. Once such air enters the sterilization box 102, it is directed through a non-linear path as directed by the positioning of the baffles 308. This is best shown in FIG. 4, which shows a top down view of the sterilization box 102 with the top cover 306 removed. As shown, the baffles 308 are positioned such that the air flow largely follows a serpentine path from the hole 204 in the top surface 306 to the exit vents 110 in the side surfaces 304. The particular manner in which the baffles 308 are positioned in FIG. 4 splits the air flow into four paths. Two of these air flow paths are shown to the right in FIG. 4, although it should be understood that two other air flow paths would be present in the left of FIG. 4, although these aren't shown for simplicity. Note that the air flow paths may not follow a strict serpentine path. For example, the baffles 308 can be positioned to create vortices 402 in the air flow paths. This effectively elongates the air flow path, which exposes air to UV radiation for a longer time, as explained further below. Baffles 404 can be positioned so as to close the air flow paths as necessary to form vortices 402, as well as to direct the air flow into the baffle structure.

To more completely sterilize the air in the air flow paths, the non-linear air flow path includes UV LED chips 406, which may be formed on LED strips 408. The UV LED chips 406 and strips 408 are shown to the left in FIG. 4, although it should be understood that UV LED chips 406 and strips 408 would also be present in the right of FIG. 4, although this isn't shown for simplicity. In the example shown, the LED strips 408 are affixed to the vertical surfaces of the baffles 308, as shown in the plan view at the bottom right in FIG. 4. In this example, there are two UV LED strips 408 spaced vertically on the walls of the baffles 308, which improves exposure of the air to UV radiation.

Preferably, as much of the non-linear air flow paths are exposed to UV radiation as possible, and so in FIG. 4 the UV LED strips 408 are essentially positioned along the entirety of the lengths of the air flow paths, and further preferably are positioned along at least half of these lengths. The width d of the air flow paths around the baffles 308 can may be approximately 1 to 1.5 inches. Assuming that the sterilization box 102 is approximately 2×2 feet, the length of each of the four air flow paths is approximately 60 to 100 inches, and thus irradiation preferably occurs for at least approximately 30 to 50 inches along these paths. Because the UV radiation may be harmful to people, it is preferable that the UV LED strips 408 not appear in positions where the UV radiation could shine or leak out of the sterilization box 102. Thus, for example, the UV LED strips 408 are not proximate the exit vents 110. UV LED strips 408 may as shown be placed on both sides of the baffles 308, which irradiates the air flow paths from opposing sides. UV LED strips 408 may be placed elsewhere as well, such as on the top side of the bottom surface 302, or the underside of the top cover 306.

Assuming that the height of the sterilization box 102 is about 4.5 inches, the total volume of each of the four air flow paths is approximately 360 cubic inches. Fan 202 may for example comprise Part No. 09225VA-12K-AA-cc, manufactured by NMB Technologies Corp., which moves air with a flow rate of 54 cubic feet/minute, which would move air through each of the four air flow paths in parallel at a flow rate of 13.5 cubic feet/minute, or 389 cubic inches/second. As such, each unit volume of air in each flow path is constantly UV irradiated for approximately one second (360/389), and with a high flux or energy density because the air is being irradiated almost continuously along the length of each air flow path. Note this is advantageous when compared with other air purification system that use UV radiation to purify air. Typically such systems involve a point UV source which the air to be sterilized rushes passed, meaning that each unit volume of air is only radiated for a short time, which may result in incomplete inactivation of pathogens. By contrast, the air is constantly irradiated in the sterilization box 102 along the non-linear paths for an extended period of time, and with a high flux or energy density, thus ensuring more complete disinfection. Of course, the extent to which air is UV irradiated could be varied by changing the flow rate of the fan 202, changing the length or volume of the air flow paths, changing the intensity and number of UV LED chips 406 used, etc.

In one example, each of the UV LED chips 406 on UV LED strips 408 produces UV radiation with a peak wavelength in the range of 200 to 280 nm, which generally corresponds to the range of UV-C wavelengths. More preferably, the UV radiation has a peak wavelength in the range of 240 to 260 nm, or in the range of 260 to 280 nm. UV radiation in this range has been shown to be particularly useful to inactivate viruses by targeting their nucleic acids. See K. Bergmann, "UV-C Irradiation: A New Viral Inactivation Method for Biopharmaceuticals," America Pharmaceutical Review, Vol 17(6) (November 2014).

While FIG. 4 shows four air flow paths each following a non-linear path, and two exit vents 110, it should be understood that this is just one example. There could be more or less air flow paths established with the sterilization box 102, or more or fewer exit vents 110. For example, a single non-linear path could comprise a spiral in which air spirals around the box at increasing diameters, until the sterilized air eventually exits the box at a single exit vent. Also, though not illustrated, the sterilization box 102 may include one or more filters configured to filter the sterilized air before it is released through the exit vents 110. For example, the filters may be configured as part of the exit vents 110 or near the exit vents. The filter(s) may be high-efficiency particulate air (HEPA) filters or charcoal filters, for example.

As shown in FIG. 4, the sterilization box 102 can include an electronics section 410. This section 410 can be walled off from the baffles 308 and the air flow paths by a wall 412. Section 410 can include driver circuitry 414 for driving the UV LED chips 406 in the sterilization box 102. Power for driving the LED chips 406 and the fan 202 may be provided by AC electricity supplied, for example, from a wall outlet. Thus, the LED driver circuitry 414 may include transformer/rectifier stages for supplying appropriate DC voltage and/or current for the LED chips and the fan. Note that such transformer and/or rectifier stages may comprise different electronic components or subcomponents, but are all considered as the driver circuitry in this application. Though not illustrated in FIG. 4, the sterilization box 102 may also (or alternatively) include a battery, such as a rechargeable battery, for providing power for the LED chips and the fan.

Electronics section 410 can include or more ports 416 which receive AC power 100 (FIG. 5) from outside the sterilization box 102, e.g., from a socket or other power source or line to which the sterilization box is connected. Electronics section 410 may also include one or more ports 418 to allow signaling to be output from driver circuitry 414 to the UV LED chips 406 in the UV sterilization box 14 and to the safety switch 312. One skilled will understand that such signaling may be connect to each of the UV LED strips 408. In this regard, it can be useful to connect the various UV LED strips 408 within the sterilization box in a manner to reduce the amount of signaling and connections required. Although not shown, the surface of the sterilization box can include a circuit board to assist in routing signaling to the UV LED strips 408. Preferably, port(s) 418 are optically blocked after the signaling has passed through to prevent UV light from entering electronics section 410. It is preferable to include the system electronics within section 410 so it can be easily accessed. For example, top cover 306 of the UV sterilization box 102 can be removed (using screws 310, FIG. 3), thus allowing access as necessary to maintain or replace system electronics. The size of electronic section 410 can vary depending on the size of the system electronics that are supported.

Figure 5:
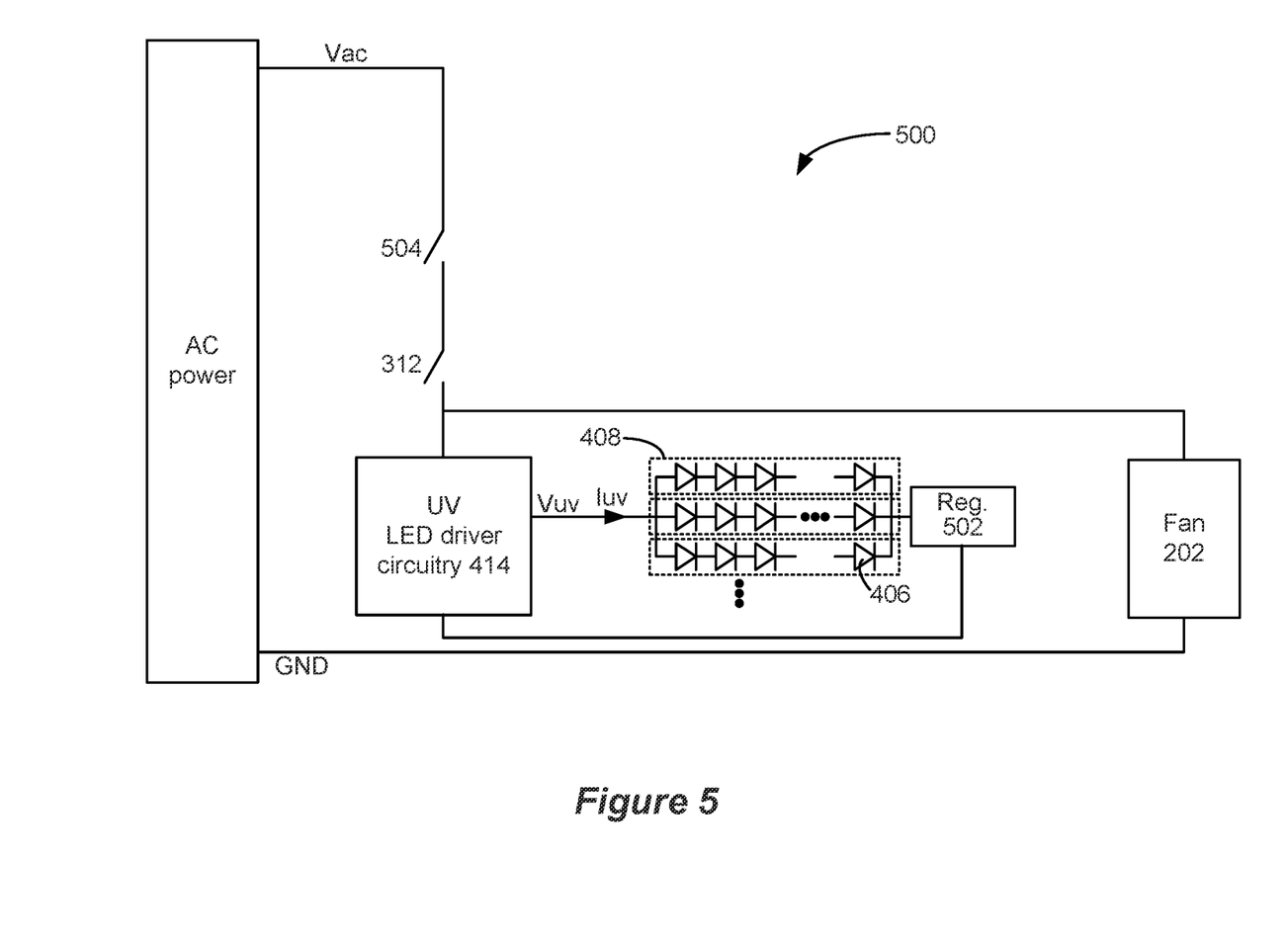
FIG. 5 shows system electronics for operating the portable disinfecting unit.

An embodiment of system electronics 500 is shown in FIG. 5. AC power provides a voltage Vac, which is provided to the UV LED driver circuitry 414, and to the fan 202. Although not shown, it should be understood that Vac may be processed (transformed, rectified to DC voltages, etc.) prior to being provided to the driver circuitry and fan in accordance with their input power needs. LED driver circuitry 414 provides a compliance voltage Vuv as necessary to provide a current Iuv necessary to drive the UV LED chips 406, with a regulator 502 controlling Iuv. The system electronics 500 may include a switch 504 for controlling the LEDs and fan. Likewise, the system electronics 500 may further include a safety switch 312. As described earlier, this switch 312 is designed to open to cut power to the UV LED chips 406 (e.g., via driver circuitry 414) when the top cover 306 is removed from the sterilization box 102. As shown, safety switch 312 is in series with switch 504, and so would also disable power to the fan 202. However, switch 312 could also be located in the circuitry to cut power to only the LED driver circuitry 414. In one example, the power required by the sterilization box 102 may comprise about 40 Watts, with the UV LED chips 406 requiring approximately 30 W, and the fan requiring about 10 W.

Figure 6:
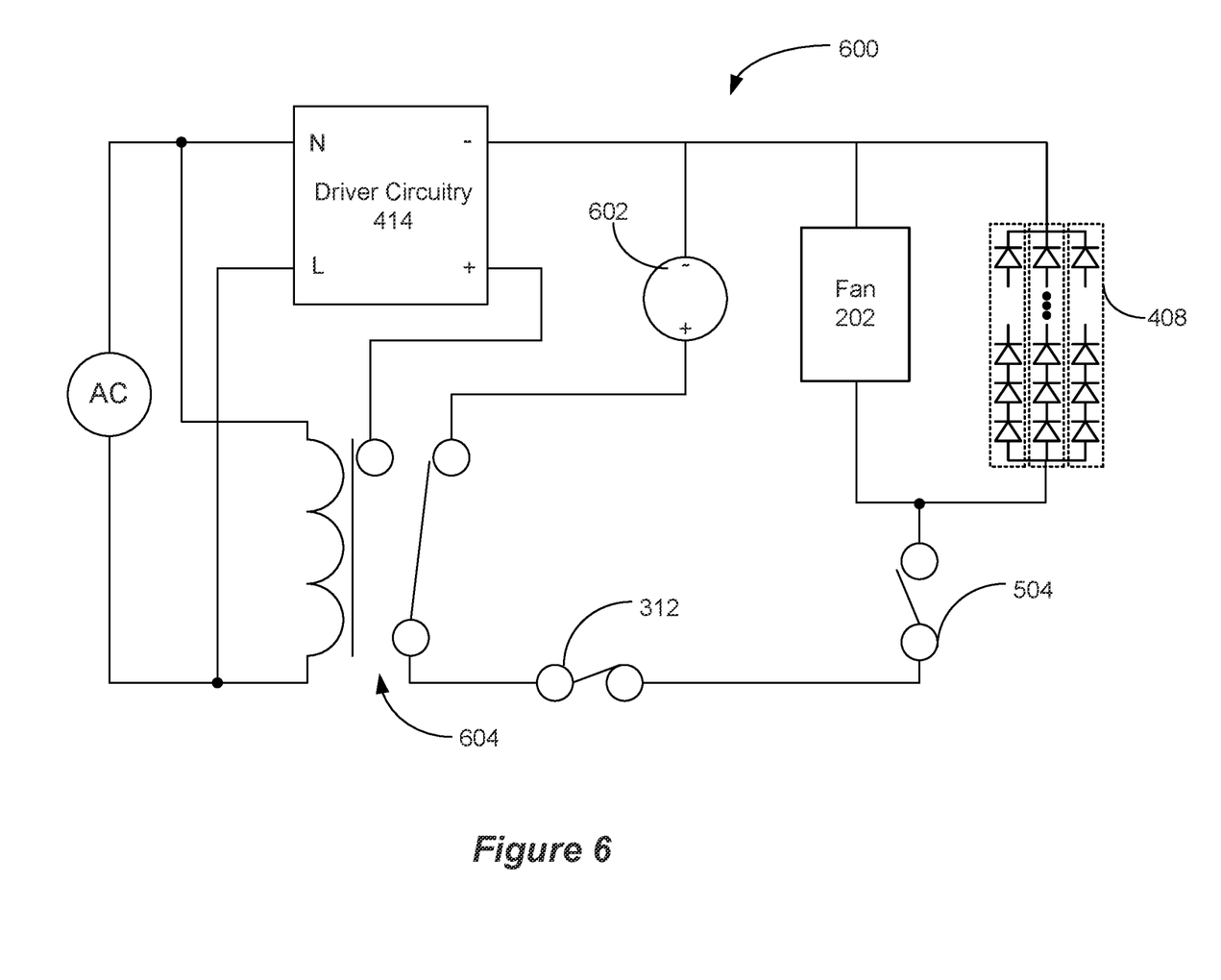
FIG. 6 shows an alternative embodiment of system electronics for operating the portable disinfecting unit.

FIG. 6 illustrates another embodiment of system electronics 600. The system electronics 600 allows the disinfecting unit to be powered using either AC power or using a battery 602. As mentioned above, the battery may be either a rechargeable battery or a primary battery. Though not shown in FIG. 6, the system electronics may include charging circuitry for recharging the battery 602 when the disinfecting unit is connected to AC power. The illustrated embodiment of the system electronics includes a relay 604, such as the illustrated single pole double throw (SPDT) relay, which is configured to automatically switch between battery power and AC power depending on whether the disinfecting unit is plugged into wall power. Other switching configurations will be apparent to a person of skill in the art. In FIG. 6, the fan 202, the UV LED strips 408, the safety switch 312, the on/off switch 504, and the LED driver circuitry 414 are as described earlier. Note that the live (L) and neutral (N) terminals of the LED driver circuitry 414 are specifically denoted in FIG. 6.

The disclosed portable disinfecting unit can be modified to include wireless communication capabilities, as described in U.S. patent application Ser. No. 17/317,656, filed May 11, 2021 (published as US 2022/0362432), a patent application which is filed concurrently herewith, and which is incorporated herein by reference in its entirety. As described in that application, providing wireless communications allows the disinfecting unit to be controlled and monitored by an application running on an external device. Further, the disinfecting unit can be responsive to a sensor system, which is also described in the above-incorporated application. This sensor system can detect one or more environmental conditions, and can use those sensed conditions to control one or more functions in the disinfecting unit, such as the fan, UV sterilization, and (if present) illumination. The sensor system may wireless communicate with the disinfecting unit. Alternatively, the sensor system can be on installed on the disinfection unit, such on the intake vent as illustrated in FIG. 1.

The embodiments of the portable disinfecting unit 100 described above do not include any lighting on the outside of the unit. However, it will be appreciated that exterior lighting, such as described in the '816 Application discussed above, could be provided on one or more of the exterior surfaces of the sterilizing box 102. For example, such exterior lights might shine down from the box or up toward the ceiling. According to some embodiments, the exterior lighting may comprise LEDs that provide illumination that have significant emission peaks at 405 nm and 470 nm. Circuitry for controlling such exterior lighting is described in the incorporated '816 Application. Moreover, the disinfecting unit may include exterior lighting to indicate various states associated with the unit. For example, green lights may indicate that the system is running, and red lights may indicate that the system is charging. In embodiments of the disinfecting unit that include environmental sensor systems various colors of lights may serve as indicators of environmental conditions inside the room.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A portable disinfection apparatus for disinfecting air in a room, the apparatus comprising:
    a portable sterilization box comprising:
        a top, an interior, a plurality of exit vents and a plurality of baffles defining a plurality of serpentine airflow paths configured to receive drawn air and to output disinfected air at one of the plurality of exit vents,
        a plurality of ultraviolet (UV) radiation sources comprising LED chips affixed to the sides of the baffles along at least a majority of a length of each of the airflow paths and configured to irradiate the drawn air with UV radiation along the airflow paths to produce heated disinfected air,
        a straight, rigid intake tube connected to the top of the sterilization box and configured to extend at least four feet above the sterilization box to draw air from a first location in a top portion of the room, and to provide the drawn air to a central portion of the interior of the sterilization box, whereby the drawn air is split into the plurality of airflow paths,
        wherein the rigid intake tube is configured to telescope up and down with respect to the sterilization box but not to articulate side-to-side with respect to the sterilization box, and
    wherein the sterilization box is configured to release the heated disinfected air into the room from the plurality of exit vents at a second location that is at least four feet lower in the room than the first location.

2. The apparatus of claim 1, further comprising a stand configured to support the portable sterilization box.

3. The apparatus of claim 2, wherein the stand comprises wheels.

4. The apparatus of claim 1, wherein the intake tube is at least six feet in length.

5. The apparatus of claim 1, wherein the intake tube is adjustable in length.

6. The apparatus of claim 1, wherein the plurality of paths are configured to create vortices in air flow along the paths.

7. The apparatus of claim 1, wherein the UV LED chips are configured to produce radiation with a peak wavelength in a range from 200 to 280 nm.

8. The apparatus of claim 7, wherein the UV LED chips are configured to produce radiation with a peak wavelength in a range from 240 to 280 nm.

9. The apparatus of claim 1, wherein the sterilization box comprises at least one filter configured to filter the drawn air.

10. The apparatus of claim 1, wherein the sterilization box is configured to operate on both AC power and on battery power.

11. A method of disinfecting air in a room, the method comprising:
    providing a portable disinfection apparatus comprising:
        a portable sterilization box comprising:
        a top, an interior, a plurality of exit vents and a plurality of baffles defining a plurality of serpentine airflow paths configured to receive the drawn air and to output disinfected air at one of the plurality of exit vents,
        a plurality of ultraviolet (UV) radiation sources comprising LED chips affixed to the sides of the baffles along at least a majority of a length of each of the airflow paths and configured to irradiate the drawn air with UV radiation along the airflow paths to produce heated disinfected air, and
        a straight rigid intake tube connected to the top of the sterilization box and configured to extend at least four feet above the sterilization box to draw air from a first location in a top portion of the room and to provide the drawn air to a central portion of the interior of the sterilization box, whereby the drawn air is split into the plurality of airflow paths,
    wherein the rigid intake tube is configured to telescope up and down with respect to the sterilization box but not to articulate side-to-side with respect to the sterilization box,
    using the portable disinfection apparatus to heat and disinfect the air, and
    releasing the heated disinfected air into the room from the plurality of exit vents at a second location that is at least four feet lower in the room than the first location.

12. The method of claim 11, wherein the first location is at least six feet higher than the second location.

13. The method of claim 11, wherein the UV radiation sources are configured to produce radiation with a peak wavelength in a range from 200 to 280 nm.

14. The apparatus of claim 1, wherein the portable sterilization box comprises four serpentine paths.

* * * * *